United States Patent
Choy et al.

(10) Patent No.: US 7,572,458 B2
(45) Date of Patent: Aug. 11, 2009

(54) BORON COMPOUND-LAYERED DOUBLE HYDROXIDE NANOHYBRID, METHOD OF PREPARING THE BORON COMPOUND-LDH NANOHYBRID, AND PHARMACEUTICAL COMPOSITION COMPRISING THE BORON COMPOUND-LDH NANOHYBRID

(75) Inventors: Jin Ho Choy, Seoul (KR); Ie Rang Jeon, Seongnam (KR); Soo Jin Choi, Seoul (KR); Jae Min Oh, Seoul (KR)

(73) Assignee: Ewha University-Industry Collaboration Foundation, Seoul (KR)

( * ) Notice: Subject to any disclaimer, the term of this patent is extended or adjusted under 35 U.S.C. 154(b) by 0 days.

(21) Appl. No.: 12/137,205

(22) Filed: Jun. 11, 2008

(65) Prior Publication Data

US 2009/0004228 A1  Jan. 1, 2009

Related U.S. Application Data

(60) Provisional application No. 60/943,148, filed on Jun. 11, 2007.

(51) Int. Cl.
*A61K 9/00* (2006.01)
*C07F 5/02* (2006.01)

(52) U.S. Cl. ............................... 424/400; 568/5; 568/6; 977/700; 977/911

(58) Field of Classification Search ................. 424/400; 568/5, 6; 977/700, 911
See application file for complete search history.

(56) References Cited

U.S. PATENT DOCUMENTS

| | | | | |
|---|---|---|---|---|
| 5,116,587 | A | * | 5/1992 | Pinnavaia et al. ...... 423/244.02 |
| 5,413,701 | A | * | 5/1995 | Gillespie et al. ............ 208/189 |
| 6,517,808 | B1 | | 2/2003 | Hawthorne et al. |
| 2002/0160969 | A1 | | 10/2002 | Schinazi et al. |
| 2003/0165426 | A1 | | 9/2003 | Miura et al. |
| 2005/0165426 | A1 | | 7/2005 | Manzo |

FOREIGN PATENT DOCUMENTS

| | | |
|---|---|---|
| WO | 9600090 A1 | 1/1996 |
| WO | 9809973 A1 | 3/1998 |
| WO | 0043401 A1 | 7/2000 |

* cited by examiner

*Primary Examiner*—Porfirio Nazario Gonzalez
(74) *Attorney, Agent, or Firm*—Rothwell, Figg, Ernst & Manbeck

(57) ABSTRACT

Provided are a boron compound-layered double hydroxide (LDH) nanohybrid in which a boron compound for boron neutron capture therapy is intercalated in between layers of LDH, a method of preparing the boron compound-LDH nanohybrid, and a pharmaceutical composition including the boron compound-LDH nanohybrid, which can be used in boron neutron capture therapy.

8 Claims, 15 Drawing Sheets

BORON COMPOUND-LAYERED DOUBLE HYDROXIDE NANOHYBRID, METHOD OF PREPARING THE BORON COMPOUND-LDH NANOHYBRID, AND PHARMACEUTICAL COMPOSITION COMPRISING THE BORON COMPOUND-LDH NANOHYBRID

CROSS-REFERENCE TO RELATED PATENT APPLICATIONS

This application claims the benefit of U.S. Provision Application No. 60/943,148, filed on Jun. 11, 2007, in the USPTO, the disclosure of which is incorporated herein in its entirety by reference.

BACKGROUND OF THE INVENTION

1. Field of the Invention

The present invention relates to a boron compound-layered double hydroxide (LDH) nanohybrid, and more particularly, to a stable boron compound-LDH nanohybrid that can be effectively used in boron neutron capture therapy, a method of preparing the boron compound-LDH nanohybrid, and a pharmaceutical composition comprising the boron compound-LDH nanohybrid, which can be used in boron neutron capture therapy.

2. Description of the Related Art

Boron neutron capture therapy is a type of cancer therapy. In boron neutron capture therapy, a compound containing boron-10 having affinity to a tumor is injected into a patient. When a low energy thermal or epithermal neutron beam having 0.025 eV is irradiated to the cancer, boron-10 capturing neutrons disintegrates into helium and lithium, that is, a nuclear fission reaction occurs, and thus high energy (unit: MeV) alpha particles ($^4He^{2+}$) that are very affective to biomolecules are emitted. The alpha particles emitted as a result of the nuclear fission reaction can selectively remove cancer cells to treat cancer. FIG. 1 is a schematic view illustrating a principle of the boron neutron capture therapy described above. Boron neutron capture therapy is used primarily for malignant glioblastoma multiforme and malignant melanoma that is a skin cancer, and, currently, research into use of boron neutron capture therapy on other types of cancer is being carried out.

If boron with a certain concentration is selectively delivered to a tumor cell, as maintaining at low levels of cytotoxicity, only cancer cells can be removed when exposed to neutrons irradiated from outside the body. A boron atom is not radioactive before it captures neutrons and also, neutrons themselves are harmless to the body. Therefore, before a boron atom captures neutrons, various factors can be changed to increase a cancer treatment effect. In this regard, various academic and medical research is being actively performed.

A boron neutron capture therapeutic agent may have various characteristics according to the site of a tumor. For example, a boron neutron capture therapeutic agent having high concentrations of boron should be stable, be able to easily enter a tumor cell, and be harmless to the body, and have a selective targeting effect with respect to a specific cancer tissue. To obtain a boron neutron capture therapeutic agent satisfying the requirements described above, research for various boron compounds and carriers for the delivery thereof have been carried out.

Until now, many boron neutron capture therapeutic agents have been developed. For example, US 2005/0165426A1 entitled "Carboranylporphyrins and uses thereof" discloses a carrier prepared by combining a boron compound with tetraphenylporphyrin compounds, wherein the carrier can be used in boron neutron capture therapy and photodynamic therapy, US 2003/0165426A1 entitled "Use of novel metalloporphyrins as imageable tumor-targeting agents for radiation therapy" discloses halogenated porphyrins having a carborane cage, and U.S. Pat. No. 6,517,808 entitled "Methods for boron delivery to mammalian tissue" discloses a carrier prepared by encapsulating boron compounds in the bilayer of a liposome. In addition, according to US 2002/0160969A1, nucleosides and oligonucleotides are introduced to a boron compound in order to increase affinity with respect to a tumor cell; WO 98/09973 entitled "Boron-containing amino carboxylic acid compounds and uses thereof" discloses a stable boron-substituted aromatic hydrocarbon linked to an amino carboxylic acid; and WO 96/00090 entitled "Boron-containing hormone analogs and methods of their use in imaging or killing cells having hormone receptors" discloses a novel compound prepared by attaching a specific ligand to a boron compound in order to selectively accumulate the boron compound at the site of a cell related to a specific hormone. Furthermore, WO00/43401 entitled "Boron steroid mimics and pharmaceutical compounds" discloses boron heterocycle steroid mimics for treating cancer cells.

As described above, research into boron neutron capture therapeutic agents is ongoing. Specifically, ligands or nucleic acids, which are reactive to a specific cell, are attached to a boron compound to obtain selectivity with respect to a specific cancer cell. In addition, carriers for effectively delivering a large amount of boron to cancer cells are being developed. However, any inorganic drug carrier for delivering a boron compound has not yet been developed.

In addition, conventional methods described above are not effective for performing boron neutron capture therapy. Therefore, there is a need to develop a method of sufficiently improving the cell membrane permeability and selectivity of a boron compound with respect to cancer cells.

Meanwhile, a layered double hydroxide (LDH), also known as a hydrotalcite mimic compound, has a structure similar to hydrotalcite having a layered double hydroxide structure formed of zinc and aluminum, wherein zinc and aluminum are substituted with other divalent or trivalent metal. LDH has a positive charge due to the presence of trivalent metallic ions in between layers of LDH, and thus various anions can be introduced between the layers. However, LDH has not been used as a drug carrier of a boron compound that is used in a specific radioactive cancer therapy, such as boron neutron capture therapy.

SUMMARY OF THE INVENTION

The inventors of the present invention studied how to effectively treat a tumor with various boron compounds for boron neutron capture therapy and found that when a boron compound is hybridized with LDH by being intercalated in between layers of LDH, the cell membrane permeability and selectivity of the boron compound with respect to cancer cells are significantly improved and thus, the level of cytotoxicity with respect to normal cells is significantly decreased and the boron compound can be effectively used even in a small amount in the boron neutron capture therapy.

The present invention provides a novel boron compound-layered double hydroxide (LDH) nanohybrid that can be effectively used even in a small amount in a boron neutron capture therapy.

The present invention also provides a method of preparing the novel boron compound-LDH nanohybrid.

The present invention also provides a pharmaceutical composition comprising the novel boron compound-LDH nanohybrid, which can be used for a boron neutron capture therapy.

According to an aspect of the present invention, there is provided a nanohybrid of a boron compound with non-toxic layered double hydroxide (LDH), wherein the boron compound is hybridized by being intercalated in between layers of the LDH.

According to an aspect of the present invention, there is provided a method of preparing the nanohybrid, the method including: dissolving the boron compound for boron neutron capture therapy in a base solution; and adding dropwise an aqueous solution comprising a bivalent metal salt and a trivalent metal salt to the resultant boron solution until a pH of the resultant solution is in a range of 7 to 9.

According to an aspect of the present invention, there is provided a pharmaceutical composition for boron neutron capture therapy, including the nanohybrid

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
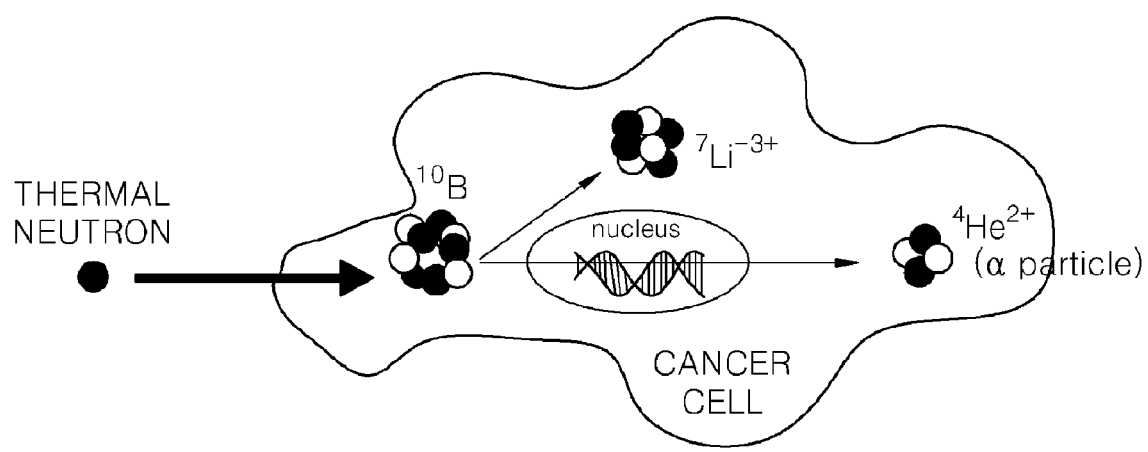
FIG. 1 is a schematic view illustrating a principle of boron neutron capture therapy.

The present invention will now be described more fully with reference to the accompanying drawings, in which exemplary embodiments of the invention are shown.

A nanohybrid of a boron compound with non-toxic layered double hydroxide (LDH) according to the present invention comprises a boron compound hybridized by being intercalated in between layers of the LDH.

The LDH of the boron compound-LDH nanohybrid includes at least one bivalent metal and at least one trivalent metal. The bivalent metal may be selected from the group consisting of $Mg^{2+}$, $Ca^{2+}$, $Zn^{2+}$, and a combination thereof, but is not limited thereto. The trivalent metal may be selected from the group consisting of $Al^{3+}$, $Fe^{3+}$, and a combination thereof, but is not limited thereto. The LDH may be any LDH known to the art that is harmless to the human body and which does not limit the manufacture of the hybrid structure.

The boron compound that is hybridized with the LDH to form a boron compound-LDH nanohybrid may be any boron compound that has a negative charge in an aqueous solution or becomes anionic in an alkali condition, and which can be effectively used in boron neutron capture therapy. Also, the born compound may have a high concentration of boron per molecule in order to be effectively used in boron neutron capture therapy. In this regard, the boron compound may be sodium mecaptoundecahydro-closo-dodecaborate (BSH) which has been approved by the US Food and Drug Administration (FDA), borono-phenylalanine (BPA), or a carboxylic compound-containing boron compound that becomes anionic in an alkali condition, such as an o-carborane-1,2-dicarboxylic acid or a p-carborane-1,12-dicarboxylic acid. Specifically, the compounds described above except for BPA, that is, BSH, an o-carborane-1,2-dicarboxylic acid, and a p-carborane-1,12-dicarboxylic acid each include a high concentration of boron per molecule, specifically ten (10) to twelve (12) boron atoms at edges of icosahedron.

The boron compound-LDH nanohybrid according to the present invention may have a particle size of 100 to 300 nm, specifically 100 to 200 nm. When the boron compound-LDH nanohybrid has the size range described above, the boron compound-LDH nanohybrid may easily permeate into a cell, and when injected into the body, the boron compound-LDH nanohybrid does not clog capillary vessels and does not physically harm cells. When the particle size the boron compound-LDH nanohybrid is less than 50 nm, the boron compound-LDH nanohybrid may clog capillary vessels of the lungs.

A method of preparing the boron compound-LDH nanohybrid according to the present invention may comprise dissolving a boron compound for boron neutron capture therapy in a base solution and then adding dropwise an aqueous solution of bivalent and trivalent metal salts thereto until a pH of the resultant solution is in a range of 7 to 9.

The base solution may be an aqueous solution including sodium hydroxide or ammonia, wherein the concentration of the base solution may be in a range of 0.1 to 0.2 M. When the concentration of the base solution is too high, LDH may precipitate too quickly and the obtained product is too small in size or may agglomerate.

The bivalent metal salt to be added may be a bivalent metal salt for forming LDH of the boron compound-LDH nanohybrid to be prepared and may be zinc nitrate, zinc chloride, magnesium nitrate, magnesium chloride, or a mixture thereof. The trivalent metal salt to be added may be a trivalent metal salt for forming LDH of the boron compound-LDH nanohybrid to be prepared and may be aluminum nitrate, aluminum chloride, or a mixture thereof.

The method of preparing the boron compound-LDH nanohybrid will now be described in detail. First, a boron compound for boron neutron capture therapy is dissolved in a base solution until the concentration of the boron compound reaches a predetermined level. Then, an aqueous solution of bivalent and trivalent metal salts is added dropwise thereto until a pH of the resultant solution is in a range of 7 to 9, thereby precipitating a boron compound-LDH nanohybrid according to the present invention. In this regard, formation of LDH and hybridization of the boron compound with LDH occur at the same time. When the pH of the resultant solution is less than 7, the boron compound-LDH nanohybrid may not be formed and a hydroxide of a trivalent metal may precipitate. On the other hand, when the pH of the resultant solution is greater than 9, the boron compound-LDH nanohybrid may not be formed and a hydroxide of a bivalent metal may precipitate.

The boron compound-LDH nanohybrid according to the present invention may have various compositions, particle shapes, and particle sizes, according to conditions of the method described above, such as the concentration of metal ions, the ratio of metal ions, the adding speed of the aqueous solution of bivalent and trivalent metal salts, and the total reaction time. As described above, according to the particle size the boron compound-LDH nanohybrid according to the present invention, the boron compound-LDH nanohybrid may clog capillary vessels or capillary vessels of the lungs of the body into which the boron compound-LDH nanohybrid is injected, thereby causing toxicity in the body. Accordingly, it is important to obtain a boron compound-LDH nanohybrid having appropriate uniform sizes in the process for preparing boron compound-LDH nanohybrid according to the present invention. As described above, the particle size the boron compound-LDH nanohybrid according to the present invention may be in a range of 100 to 300 nm, specifically in a range of 100 to 200 nm. To obtain a boron compound-LDH nanohybrid having the size range described above, the reaction time, that is, a time period during which the aqueous solution of the bivalent and trivalent metal salts is added dropwise to the base solution of a boron compound to precipitate a boron compound-LDH nanohybrid, may be in a range of 20 to 24 hours. Also, the concentration of the aqueous solution of bivalent and trivalent metal salts may be in a range of 0.1 to 0.2 M, and a ratio of the bivalent metal to the trivalent metal, specifically a ratio of Zn to Al may be in a range of 1.8 to 2.2, and the adding speed of the aqueous solution of bivalent and trivalent metal salts may be in a range of 15 to 20 µl/second.

The boron compound-LDH nanohybrid according to the present invention may have a higher level of cell membrane permeability and a higher level of selectivity with respect to cancer cells than a free boron compound that is not hybridized, and thus the amount of the boron compound required to be effectively used in a boron neutron capture therapy without cytotoxicity can be reduced. Also, the boron compound is intercalated in between layers of LDH and thus, stability of the boron compound can be improved.

A pharmaceutical composition for boron neutron capture therapy according to the present invention includes the boron compound-LDH nanohybrid.

Figure 2:
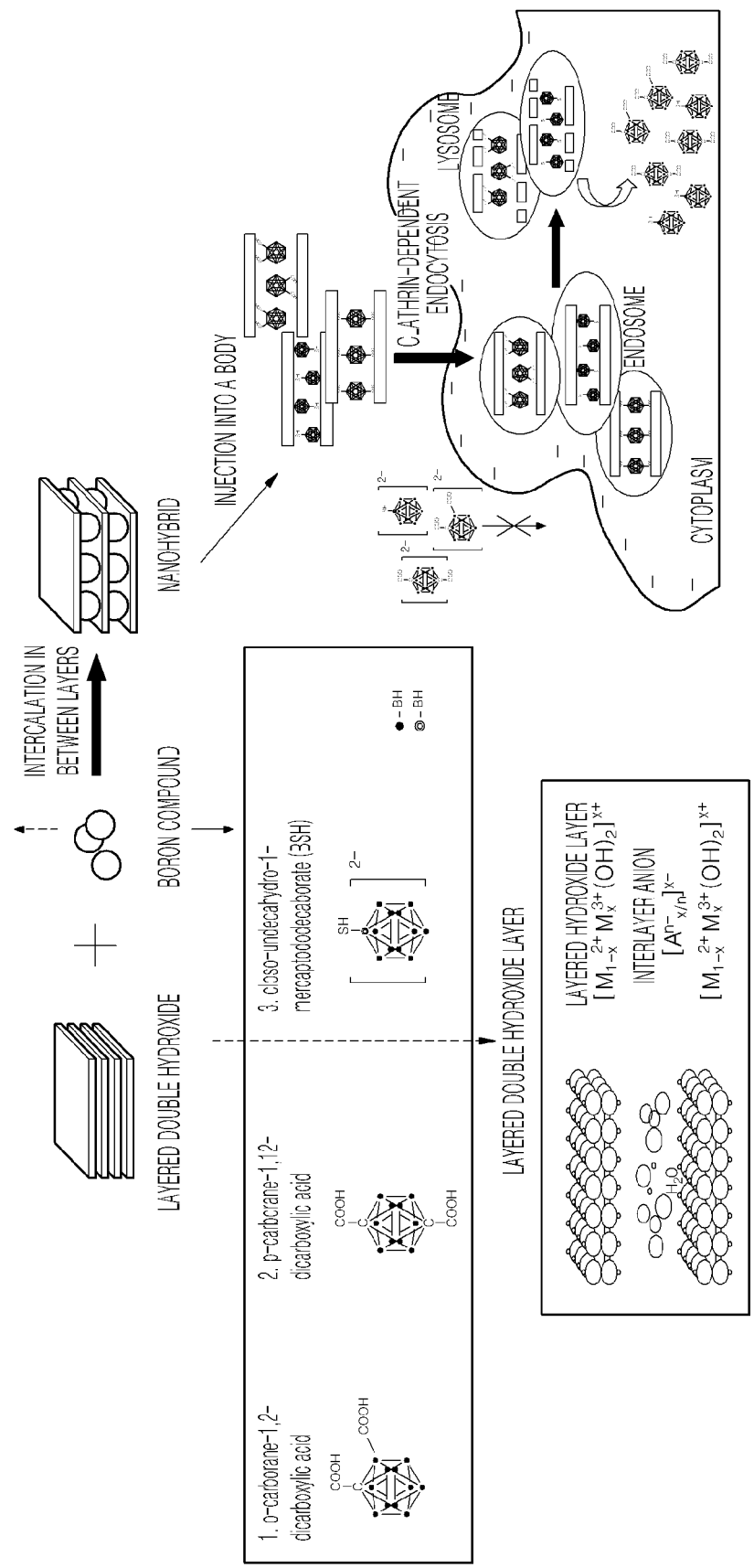
FIG. 2 is a schematic view illustrating a boron compound-layered double hydroxide (LDH) nanohybrid permeating into a cancer cell, with a high level of cell membrane permeability.

FIG. 2 is a schematic view illustrating a boron compound-LDH nanohybrid permeating into a cancer cell, with a high level of cell membrane permeability. Referring to FIG. 2, the boron compound hybridized by being intercalated in between layers of LDH can easily pass through a cell membrane due to clathrin-dependent endocytosis. On the other hand, a free boron compound that is not hybridized with LDH and exists independently can not easily enter the inside of a cell. Such high cell membrane permeability of the boron compound-LDH nanohybrid according to the present invention was identified by a cell permeation test performed on the boron compound-LDH nanohybrid with respect to cancer cells in Examples below.

The pharmaceutical composition for boron neutron capture therapy according to the present invention can be used to treat tumors in the same manner as conventional boron neutron capture therapy. That is, the pharmaceutical composition according to the present invention is injected into the body and then neutrons are irradiated thereto.

The pharmaceutical composition for boron neutron capture therapy according to the present invention may further comprise, in addition to the boron compound-LDH nanohybrid, conventional pharmaceutically acceptable additives that are used for an injection. The pharmaceutically injectable additives may include a dissolving auxiliary, a buffer, a stabilizer, a pain-relieving agent, and a preserving agent.

The pharmaceutical composition for boron neutron capture therapy according to the present invention is effective for treating all kinds of malignant tumors that can be effectively treated by boron neutron capture therapy. For example, the pharmaceutical composition can be used to treat malignant glioblastoma multiforme and malignant melanoma which is a skin cancer.

The pharmaceutical composition for boron neutron capture therapy according to the present invention has a higher level of selectivity and a higher level of cell membrane permeability with respect to cancer cells than when a boron compound is not intercalated in between layers of LDH, and thus, the content of a boron compound required in boron neutron capture therapy is less than when the boron compound is not hybridized. A dosage of the pharmaceutical composition may differ according to of the type of disease, the level of development of disease, or the gender, weight, or race of a patient. For example, the dosage of the pharmaceutical consumption administered to an average adult male may be in a range of 5 mg/kg to 15 mg/kg in the level of the boron amount. However, the boron dosage may differ according to prescription of a physician.

The present invention will be described in further detail with reference to the following examples. These examples are for illustrative purposes only and are not intended to limit the scope of the present invention.

EXAMPLES

Boron compound-layered double hydroxide (LDH) nanohybrids were prepared according to an embodiment of the present invention, and the physical and chemical structure of the obtained boron compound-LDH nanohybrids were identified with an X-ray diffractometer and an ultra violet spectrometer. The particle shape and particle size the boron compound-LDH nanohybrids were identified with a scanning electron microscope (SEM).

All cell experiments were performed with U-343 and U-87 brain cancer cells, and cytotoxicity experiments of the obtained boron compound-LDH nanohybrids were carried out through an MTT assay.

Cell membrane permeability was identified by inductively coupled plasma atomic emission spectroscopy. Specifically, each cell was treated with the boron compound-LDH nanohybrids and a free boron compound and then the concentration of boron in the cell was measured at predetermined time intervals wherein the content of boron in the boron compound-LDH nanohybrids was equal to the content of boron in the free boron compound. In general, a neutron capturing reaction is dependent upon the concentration of boron within a cancer cell, and thus, the higher the level of cell membrane permeability, the better the treatment effect of the therapeutic agent. Accordingly, the concentration of boron within a cell should be regarded as an important factor.

Example 1

Boron compound-LDH nanohybrids were prepared using the following method. This experiment was performed with three kinds of boron compounds: sodium mecaptoundecahydro-closo-dodecaborate (BSH), o-carborane-1,2-dicarboxylic acid(o-CB), and p-carborane-1,12-dicarboxylic acid(p-CB). Each boron compound was dissolved in 0.1 M sodium hydroxide solution such that the molar content of the boron compound was 1.3 times greater than that of aluminum. Then, 0.5 M metal salt solution prepared by mixing a zinc nitrate and an aluminum nitrate in a ratio of 2:1 in distilled water was slowly added dropwise to the obtained boron compound solution until a pH of the resultant solution was 8. Then, the reaction was performed at room temperature for 24 hours and the obtained precipitate was dried to obtain each boron compound-LDH nanohybrid according to the present invention.

Figure 3A:
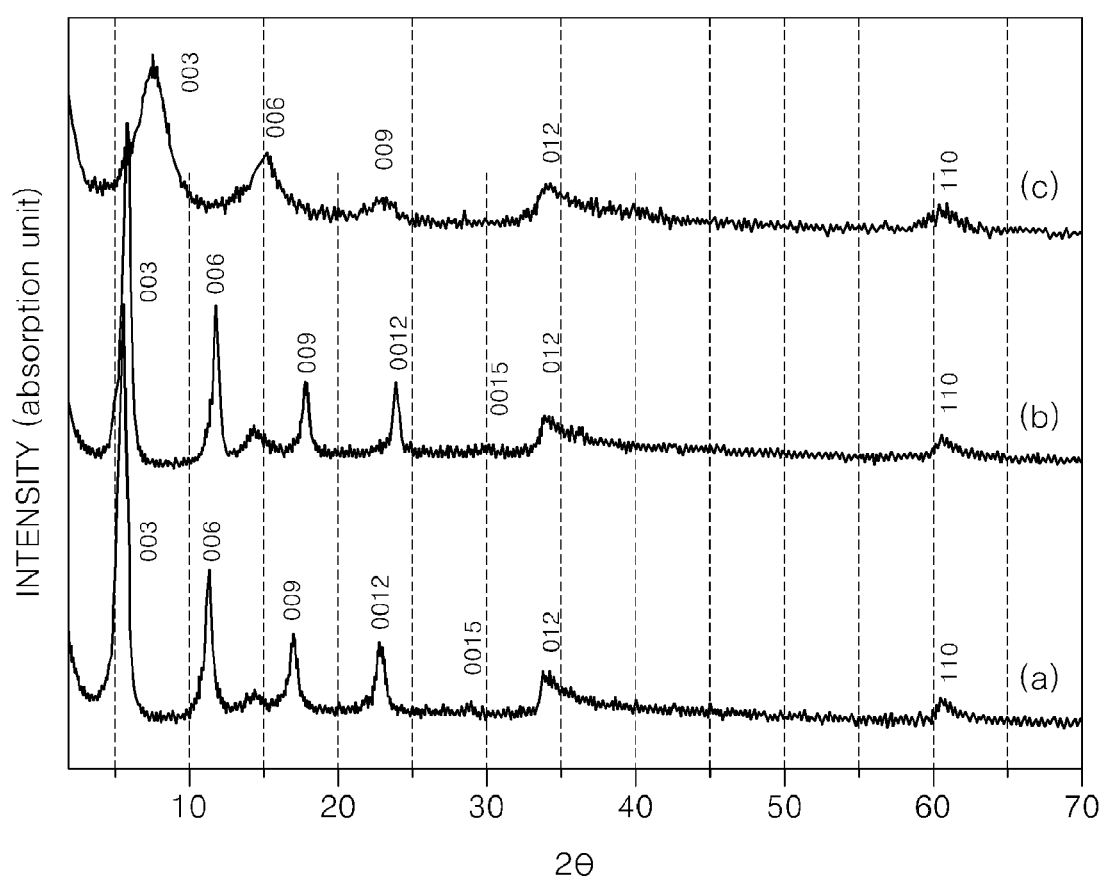
FIG. 3A shows X-ray diffraction patterns of boron compound-LDH nanohybrids prepared according to an embodiment of the present invention (a: BSH-LDH, b: p-CB-LDH, and c: o-CB-LDH)

FIG. 3A shows X-ray diffraction patterns of the obtained boron compound-LDH nanohybrids (a: BSH-LDH, b: p-CB-LDH, and c: o-CB-LDH).

Figure 4:
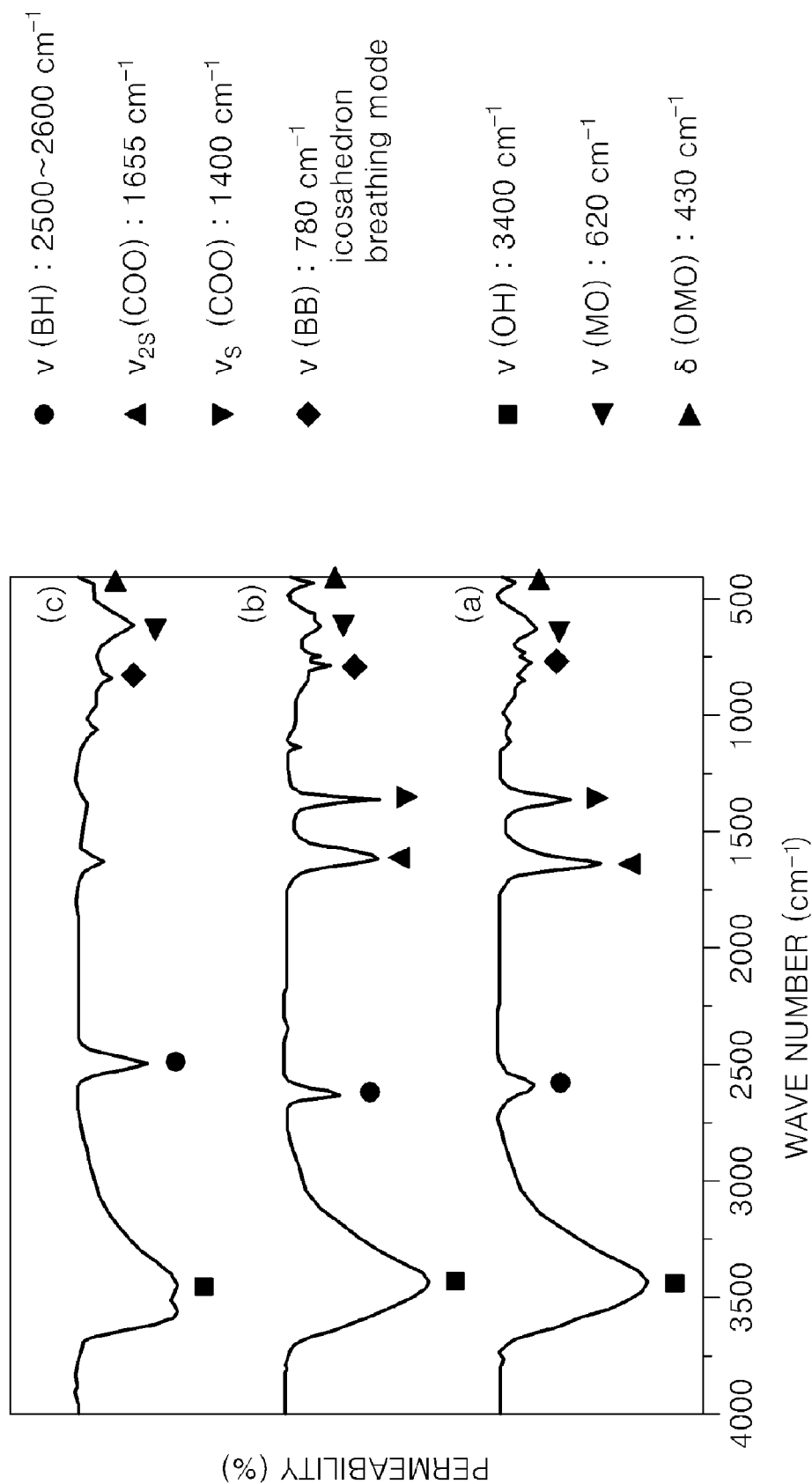
FIG. 4 illustrates ultra-violet spectroscopic spectra of boron compound-LDH nanohybrids prepared according to an embodiment of the present invention.

FIG. 4 shows results of ultra-violet spectroscopy analysis performed on the obtained boron compound-LDH nanohybrids.

Figure 3B:
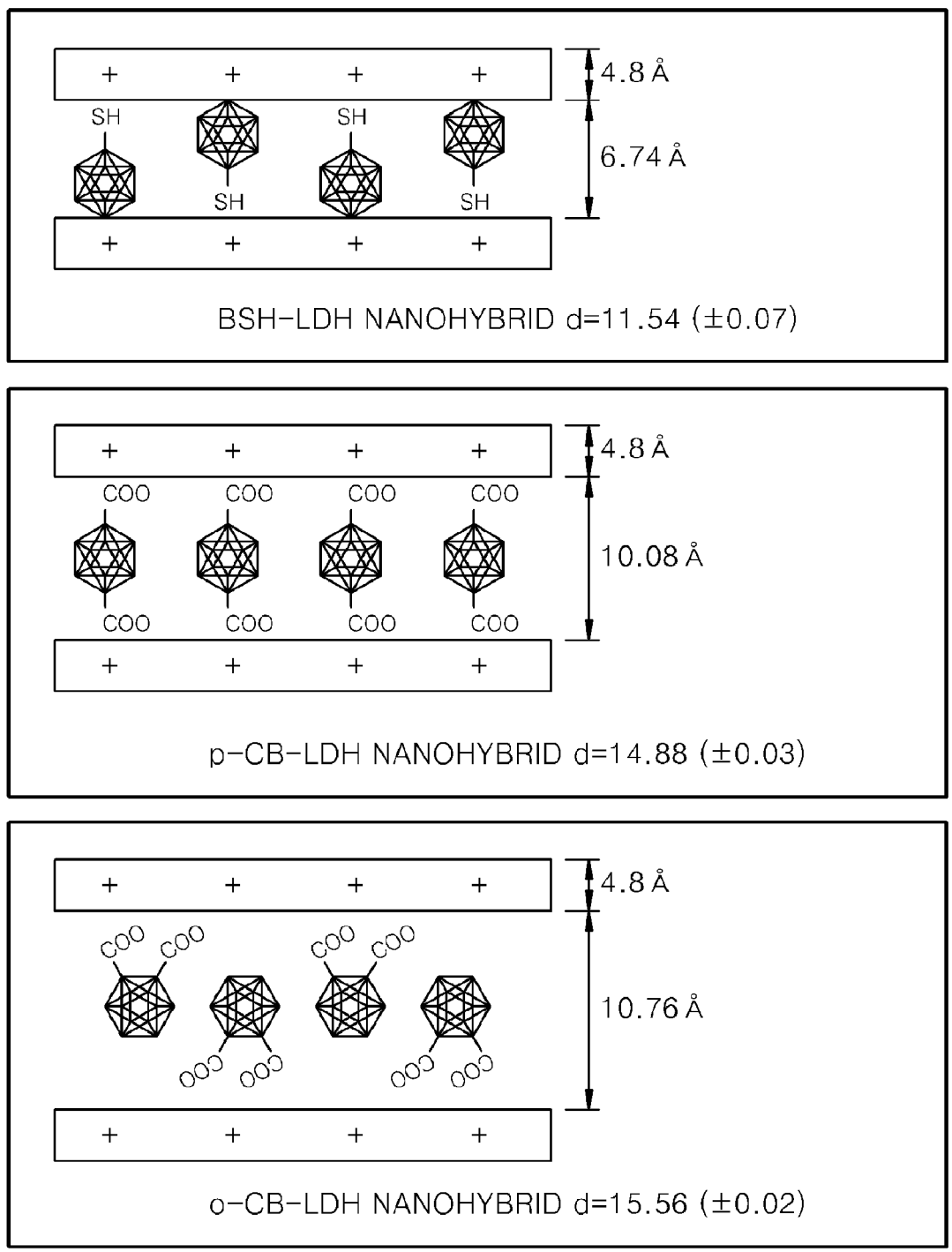
FIG. 3B illustrates the schematic structure of boron compound-LDH nanohybrids prepared according to an embodiment of the present invention.

FIG. 3B illustrates the schematic structure of the boron compound-LDH nanohybrids derived from the X-ray diffraction patterns and the UV spectroscopy analysis results. Each of the boron compound-LDH nanohybrids had a layered structure, and all the boron compounds were intercalated in between layers. In addition, during the hybridization process, each boron compound was not chemically modified except that a carboxylic acid of the boron compound lost a hydrogen atom, in order to be present in a state of an acid.

Figure 5:
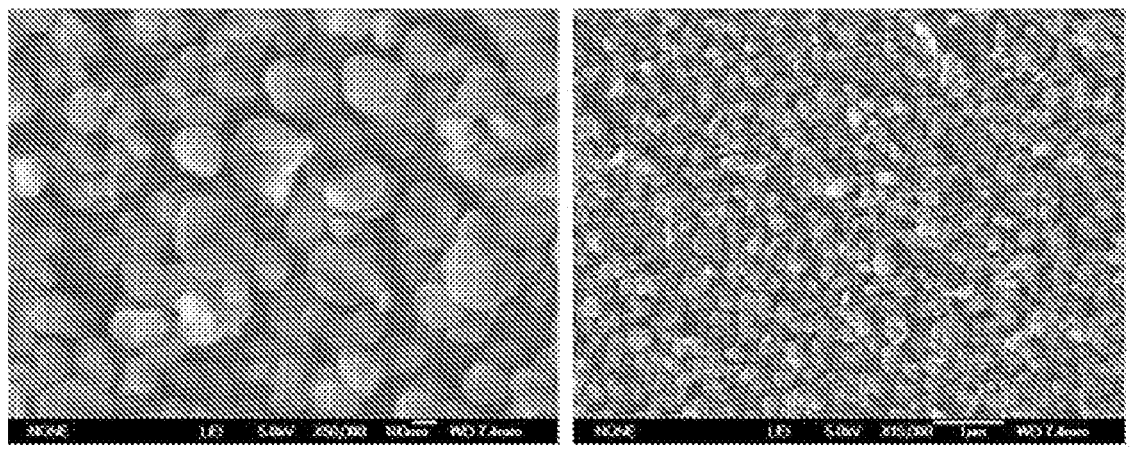
FIG. 5 shows scanning electron microscopic (SEM) images of boron compound-LDH nanohybrids prepared according to an embodiment of the present invention.

FIG. 5 is a scanning electron microscopic (SEM) image showing the particle shape and particle size the BSH-LDH nanohybrid. Referring to FIG. 5, the BSH-LDH nanohybrid has a uniform shape, and a uniform particle size 300 nm or less.

Example 2

Cytotoxicity of the boron compound-LDH nanohybrids prepared according to Example 1 was measured by performing a tetrazolium-based colorimetric (MTT) assay. In an MTT assay, yellow MTT tetrazolium salt is reduced into a purple formazan crystal by reductase enzymes in living cells, and thus, a level of suppression or facilitation of cell growth can be identified at time intervals when a cell was treated with a test compound in the presence of the MTT tetrazolium salt at time intervals. MTT assay uses such a phenomenon that the MTT tetrazolium salt reflects the suppression or facilitation of cell growth.

Figure 6A:
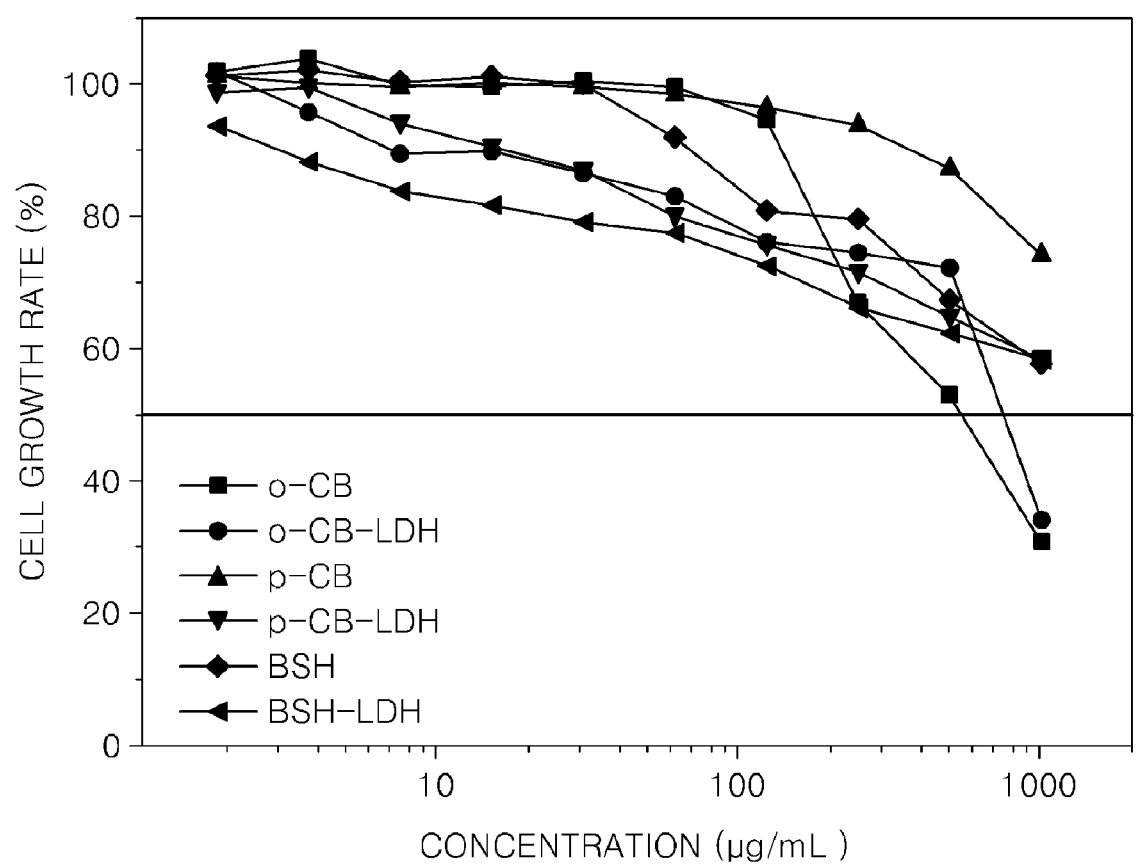
FIG. 6A shows test results of cytotoxicity to U-343 brain cancer cells of boron compound-LDH nanohybrids according to an embodiment of the present invention.
Figure 6B:
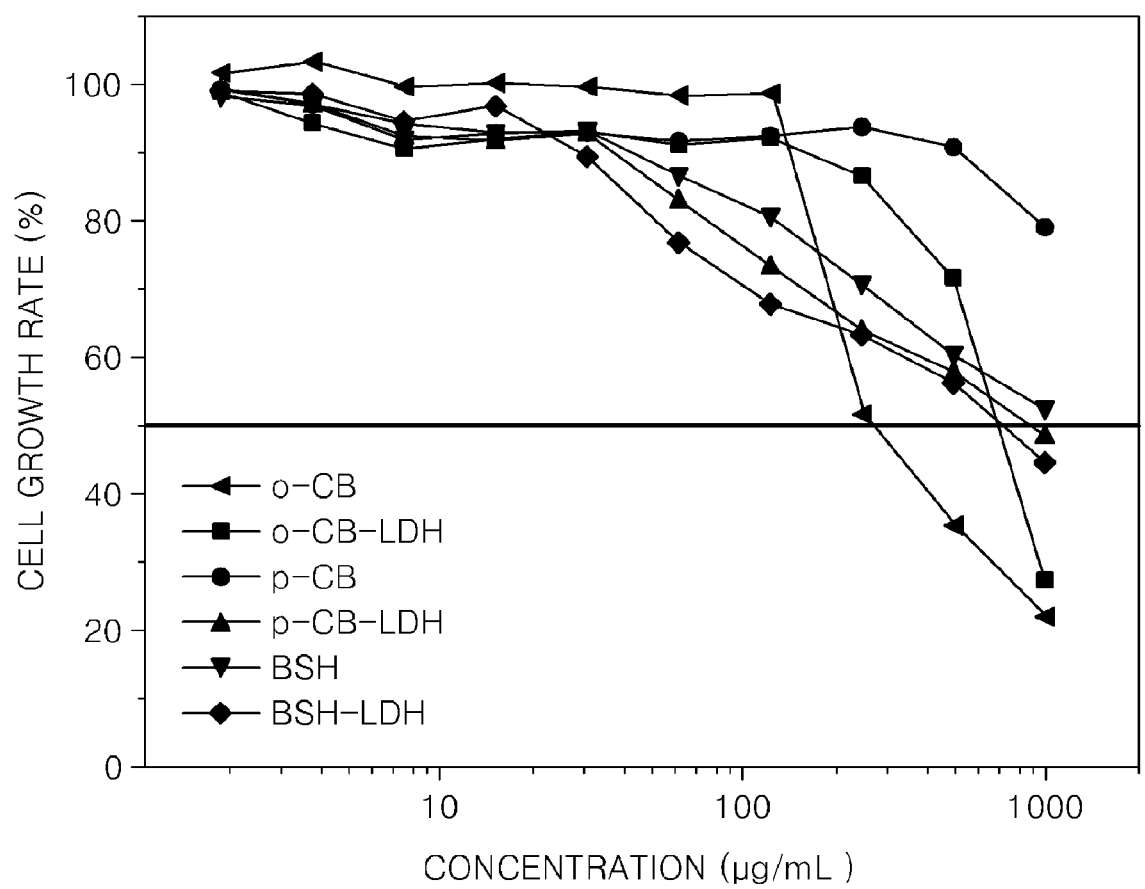
FIG. 6B shows test results of cytotoxicity to U-87 brain cancer cells of boron compound-LDH nanohybrids according to an embodiment of the present invention.

Each of a plurality of U-343 and U-87 brain cancer cells was plated on wells at a concentration of $5 \times 10^3$ cells, treated with the boron compound-LDH nanohybrids prepared according to Example 1 or free boron compound at a predetermined concentration, and then the treated cells were placed in $CO_2$ at 37° C. After 72 hours, the resultant cells were treated with a MTT labeling reagent and then 4 hours later, a surfactant was added thereto to dissolve the generated formazan. The level of the generated formazan was identified by measuring the absorption at a wavelength of 570 nm. The results are shown in FIGS. 6A and 6B. FIG. 6A shows results of the U-343 brain cancer cells, and FIG. 6B shows results of the U-87 brain cancer cells.

All the boron compounds except for o-CB did not greatly affect the cell growth and cell survival when the concentration of the boron compounds was equal to or less than 250 μg/mL, and thus, cytotoxicity thereof did not occur to any significant degree.

Figure 7A:
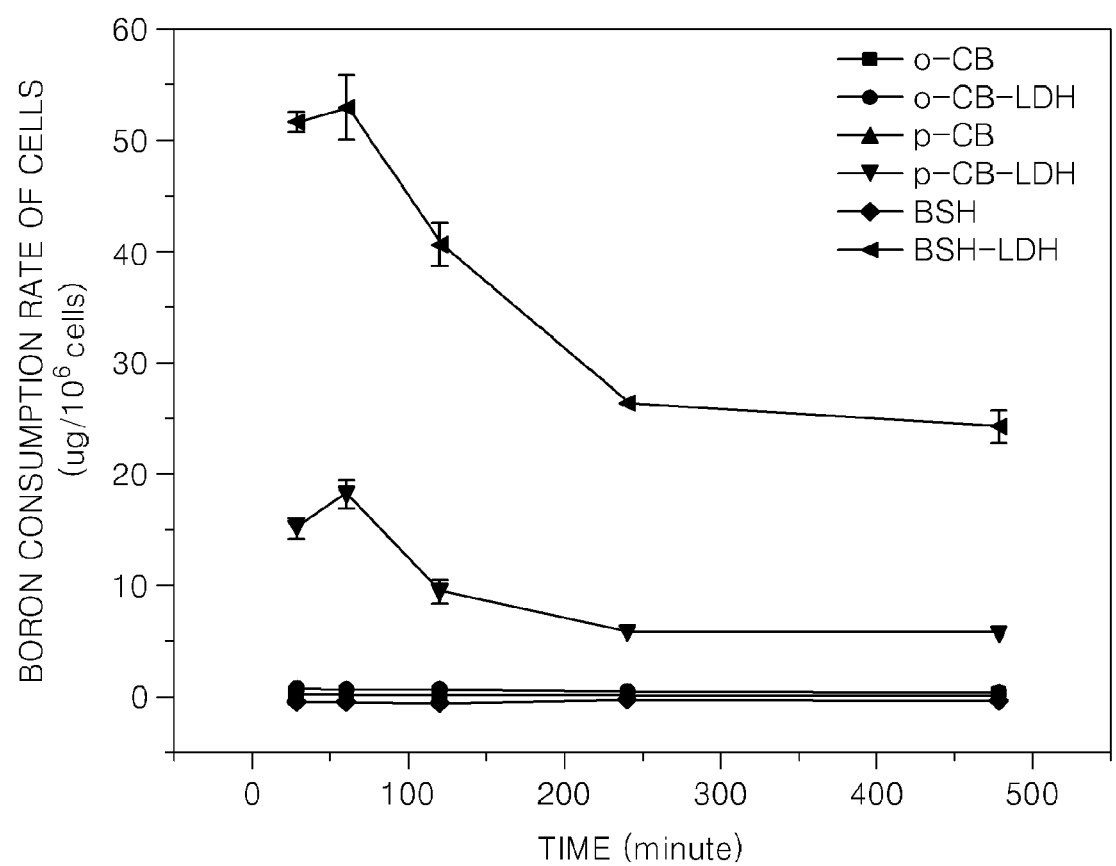
FIG. 7A is a graph of the concentration of boron accumulated in U-343 cancer cells with respect to time when U-343 cancer cells were treated with boron compound-LDH nanohybrids according to an embodiment of the present invention, wherein the concentration of boron was measured by inductively coupled plasma atomic emission spectroscopy.
Figure 7B:
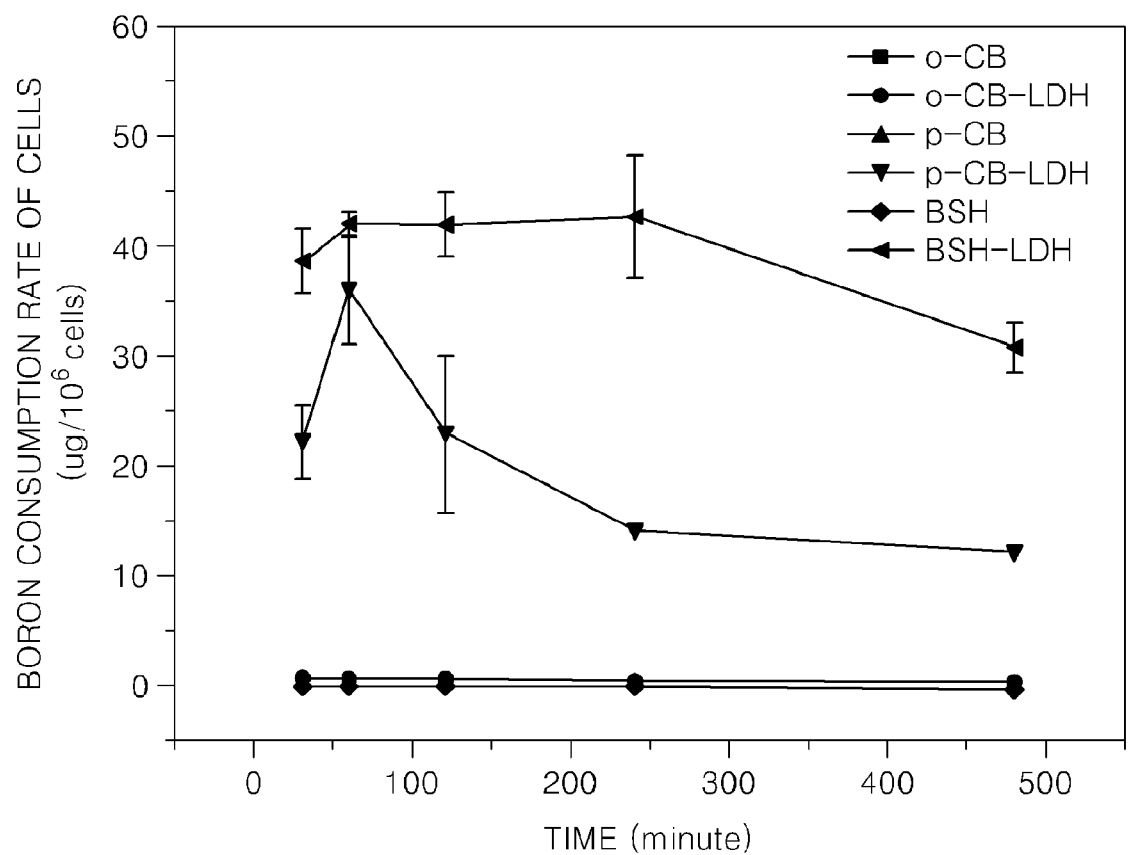
FIG. 7B is a graph of the concentration of accumulated boron in U-87 cancer cells with respect to time when U-87 cancer cells were treated with boron compound-LDH nanohybrids according to an embodiment of the present invention, wherein the concentration of boron was evaluated by inductively coupled plasma atomic emission spectroscopy.

Meanwhile, cytotoxicity was stronger when a boron compound-LDH nanohybrid of a boron compound encapsulated with LDH was used than when a free boron compound was used. This is because the boron compounds formed a boron compound-LDH nanohybrid together with LDH that is an excellent carrier, which leads to have boron compounds permeated into a cell enhanced, as illustrated in FIGS. 7A and 7B showing levels of cell membrane permeability obtained according to Example 3.

Example 3

A cell membrane permeability test was performed on the boron compound-LDH nanohybrids prepared according to Example 1. A control group was a free boron compound that was not hybridized with LDH.

U-343 and U-87 brain cancer cells were plated on a culture medium having a volume of 3 mL at a concentration of $1.5 \times 10^6$ per well, and each cell medium was treated with the boron compound-LDH nanohybrids prepared according to Example 1 and the control group, wherein the concentration of boron in each of the boron compound-LDH nanohybrids and the control group was controlled to be 60 μg/mL. After 30 minutes, 1 hour, 2 hours, 4 hours, and 8 hours, the cells were washed and dissolved with PBS and then, the resultant cells were treated with an acid and then subjected to an inductively coupled plasma atomic emission spectroscopy.

FIGS. 7A and 7B show results of the inductively coupled plasma atomic emission spectroscopy. FIG. 7A shows data of U-343 brain cancer cells, and FIG. 7B shows data of U-87 brain cancer cells.

According to boron concentration analysis results, the boron compound-LDH nanohybrids prepared according to Example 1 had very high levels of cell membrane permeability compared to the control group. After one hour, the concentration of boron in a cell was as high as 55 times greater when the boron compound-LDH nanohybrids were used than when the control group was used. In addition, a concentration of boron in a cell which was maintained for a long period of time was at least 20 times greater when the boron compound-LDH nanohybrids were used than when the control group was used. The maintained concentration was 20 μg B/$10^6$ cells, which is sufficient to remove cancer cells by boron neutron capture therapy. Also, the highest concentration of the boron compound-LDH nanohybrids in a cell was 50 μg B/$10^6$ cells, much higher than the boron concentration required to remove cancer cells by boron neutron capture therapy (0.02 μg B/$10^6$ cells).

Example 4

A test of neutron irradiation into a cell was performed with $^{10}$BSH as a free boron compound that was not hybridized with LDH and $^{10}$BSH-LDH according to Example 1. A control group was cells that were not treated with any compound and exposed to neutrons irradiation.

U-87 brain cancer cells were plated on a culture medium having a volume of 2 ml at a concentration of 1×$10^6$ cells per well, and then treated with the boron compound-LDH nanohybrids or $^{10}$BSH at boron concentrations of 30, 45, and 60 μg/mL. After one hour, the cells were washed with PBS and then, the used medium was replaced with a new medium and then neutrons were irradiated thereto. The neutron irradiation time periods were 20, 40, and 60 minutes, respectively corresponding to thermal neutron fluxes of 1×$10^{12}$ n/$cm^2$, 2×$10^{12}$ n/$cm^2$, and 3×$10^{12}$ n/$cm^2$. The survival rate of U-87 brain cancer cells was evaluated based on a colony forming ability.

Figure 8A:
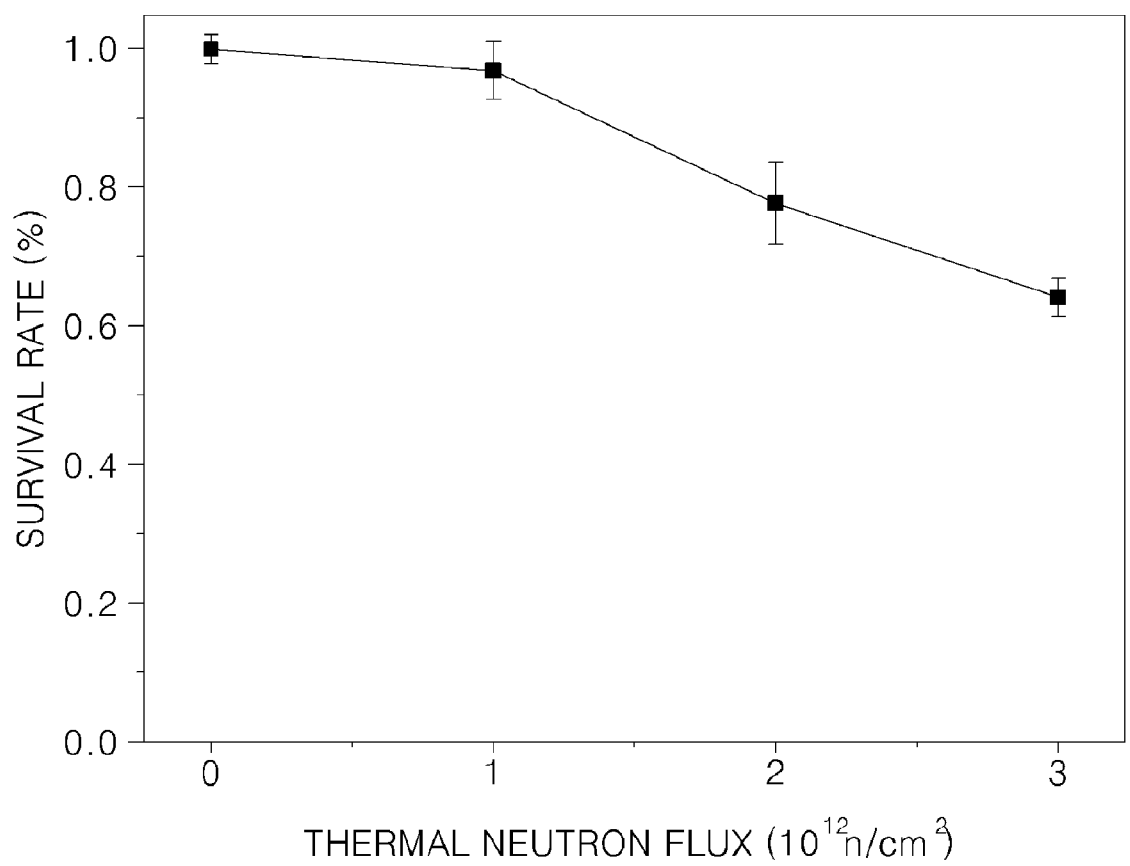
FIG. 8A is a graph of a survival rate of U-87 cancer cells when exposed to neutrons for 20 minutes, 40 minutes, and 60 minutes.
Figure 8B:
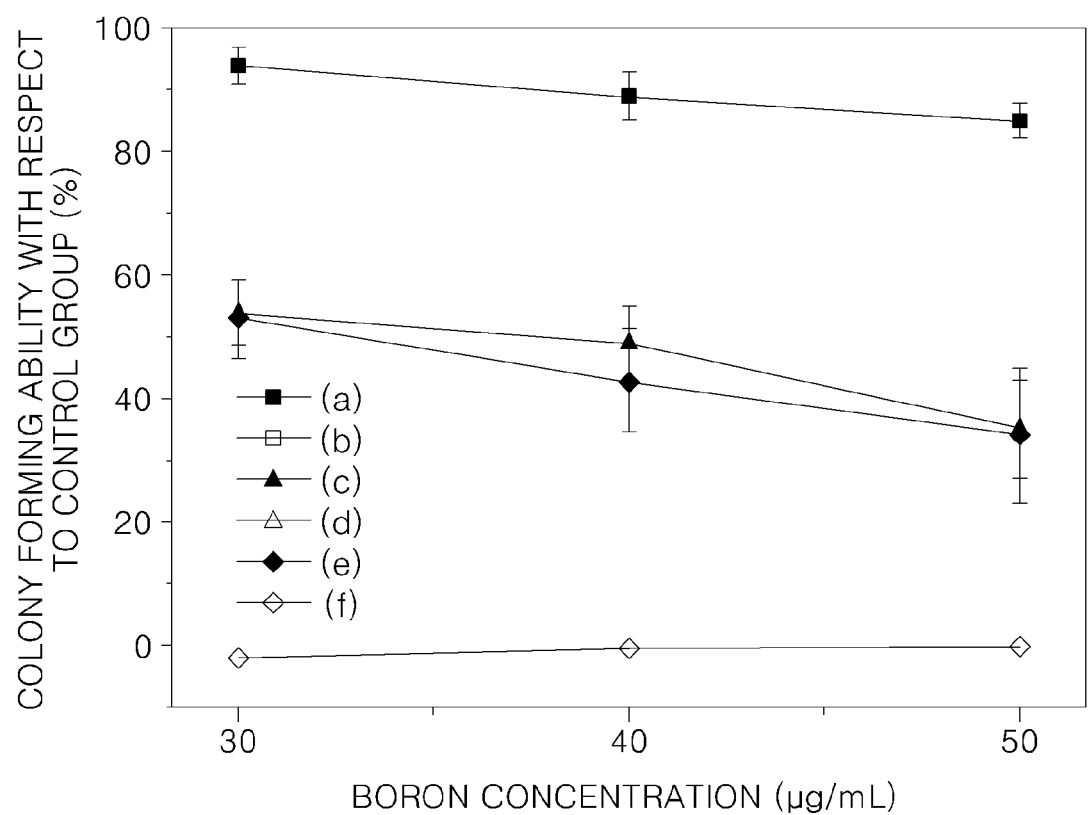
FIG. 8B is a graph of a colony forming ability of U-87 cancer cells compared to the control group when treated with $^{10}$BSH and $^{10}$BSH-LDH respectively and exposed to neutrons (a: a case in which U-87 cancer cells were treated with $^{10}$BSH and then neutrons were irradiated thereto for 20 minutes, b: a in which that U-87 cancer cells were treated with $^{10}$BSH-LDH and then neutrons were irradiated thereto for 20 minutes, c: a case in which U-87 cancer cells were treated with $^{10}$BSH and then neutrons were irradiated thereto for 40 minutes, d: a case in which U-87 cancer cells were treated with $^{10}$BSH-LDH and then neutrons were irradiated thereto for 40 minutes, e: a case in which U-87 cancer cells were treated with $^{10}$BSH and then neutrons were irradiated thereto for 60 minutes, and f: a case in which U-87 cancer cells were treated with $^{10}$BSH-LDH and then neutrons were irradiated thereto for 60 minutes)

FIGS. 8A and 8B show a survival rate of U-87 brain cancer cells for each group. Specifically, FIG. 8A shows a survival rate of U-87 brain cancer cells of the control group when exposed to neutron irradiation for 20 minutes, 40 minutes, and 60 minutes. Referring to FIG. 8A, when neutrons were irradiated for 20 minutes, the survival rate of U-87 brain cancer cells was not changed, and when neutrons were irradiated for 60 minutes, the survival rate of U-87 brain cancer cells was about 60%.

FIG. 8B is a graph of a colony forming ability of U-87 brain cancer cells when U-87 cancer cells were treated with each of $^{10}$BSH and $^{10}$BSH-LDH and then neutrons were irradiated thereto (a: a case in which U-87 cancer cells were treated with $^{10}$BSH and then neutrons were irradiated thereto for 20 minutes, b: a case in which U-87 cancer cells were treated with $^{10}$BSH-LDH and then neutrons were irradiated thereto for 20 minutes, c: a case in which U-87 cancer cells were treated with $^{10}$BSH and then neutrons were irradiated thereto for 40 minutes, d: a case in which U-87 cancer cells were treated with $^{10}$BSH-LDH and then neutrons were irradiated thereto for 40 minutes, e: a case in which U-87 cancer cells were treated with $^{10}$BSH and then neutrons were irradiated thereto for 60 minutes, and f: a case in which U-87 cancer cells were treated with $^{10}$BSH-LDH and then neutrons were irradiated thereto for 60 minutes).

Referring to FIG. 8B, when neutrons were irradiated for 20 minutes, the survival rate of U-87 brain cancer cells treated with $^{10}$BSH was similar to the survival rate of U-87 brain cancer cells that were not treated with $^{10}$BSH at all boron concentrations. When neutrons were irradiated for 40 minutes and 60 minutes, the survival rate of U-87 brain cancer cells treated with $^{10}$BSH was 45 to 55% compared to the control group at all concentrations of boron. On the other hand, when U-87 brain cancer cells were treated with $^{10}$BSH-LDH nanohybrid, the survival rate of U-87 brain cancer cells was 0 at all concentrations of boron for all the neutron irradiation time periods of 20, 40, and 60 minutes. Therefore, the cell survival rate was 0% even at low thermal neutron flux and low boron concentration.

Figure 9A:
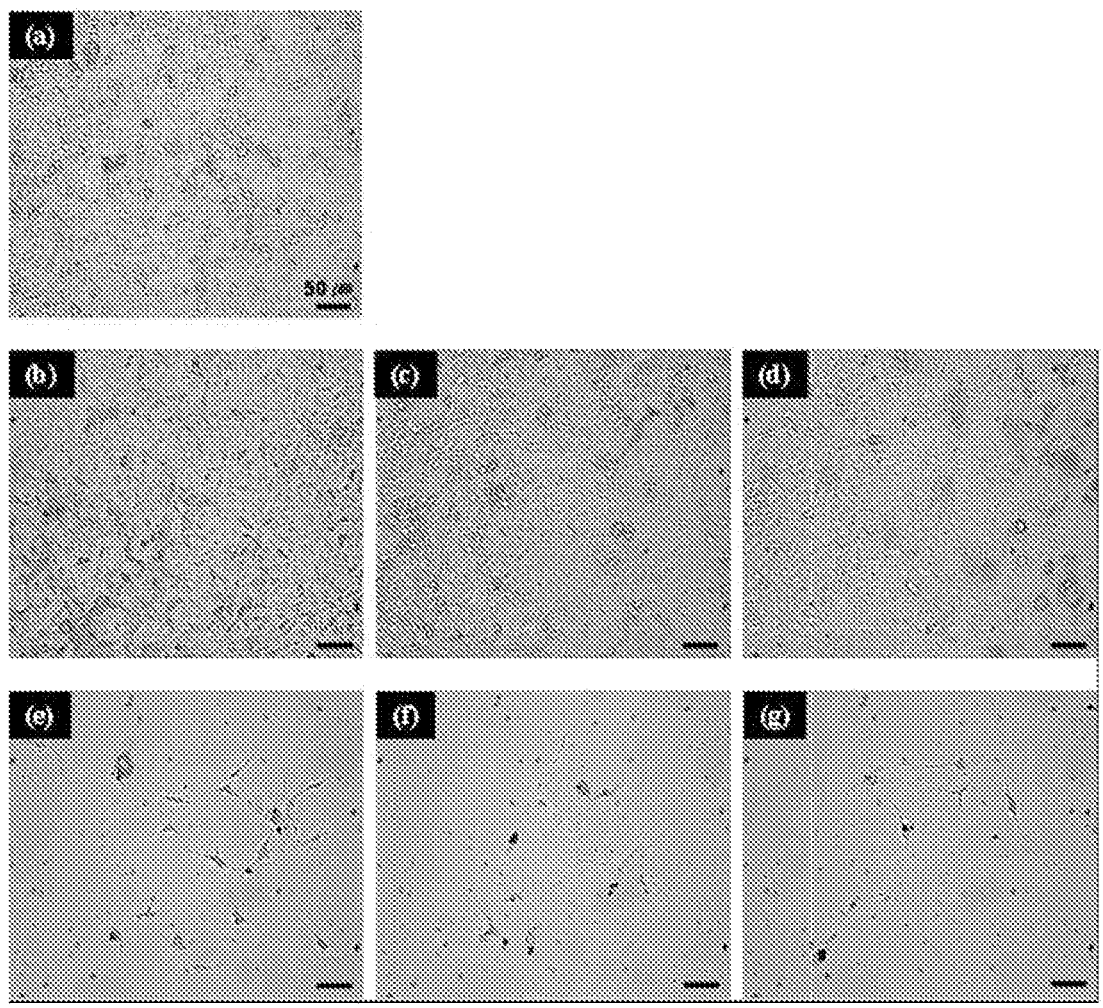
FIG. 9A shows a microscopic image of U-87 cancer cells when exposed to neutrons for 20 minutes ($1\times10^{12}$ n/cm$^2$)
Figure 9B:
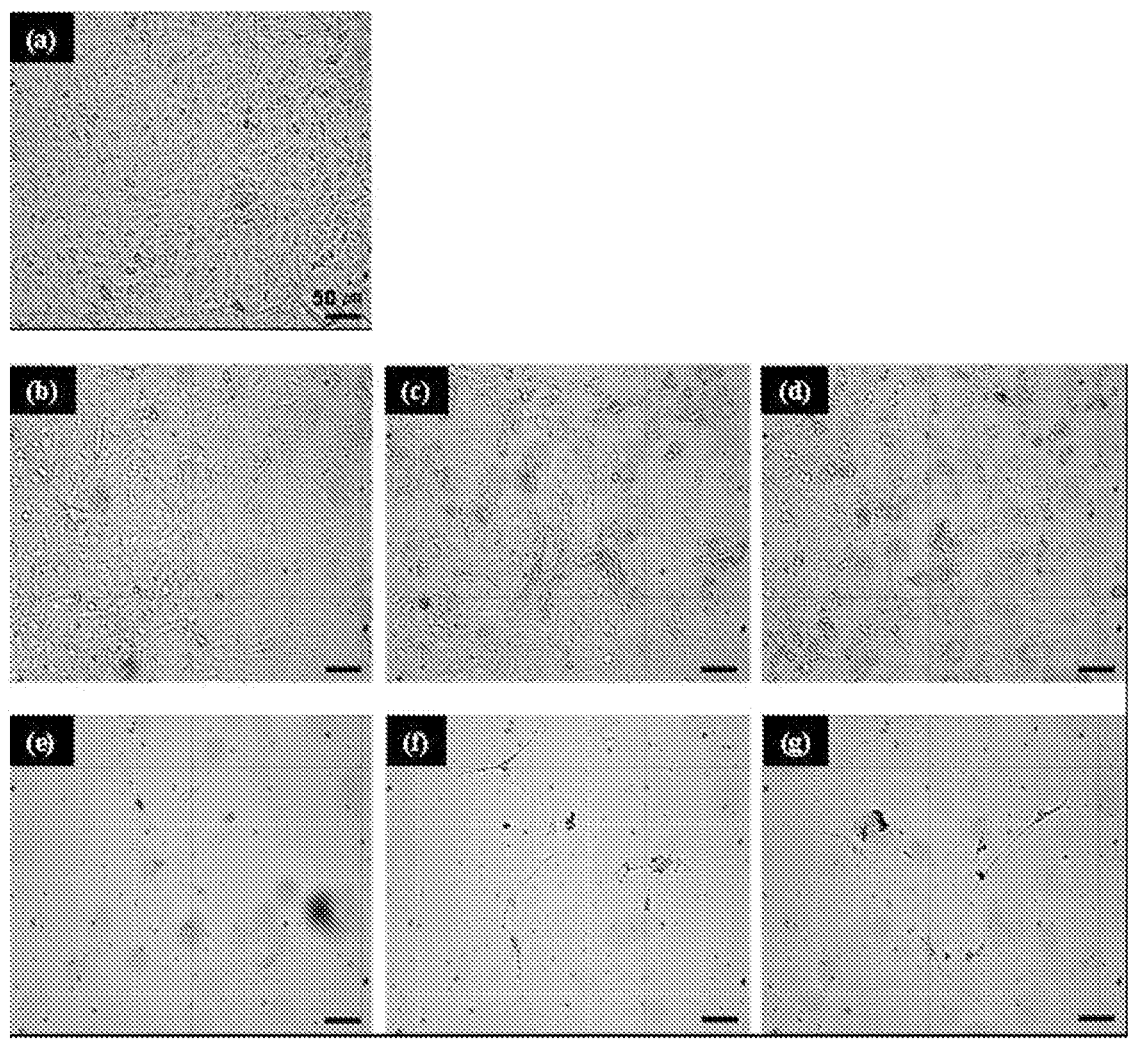
FIG. 9B shows a microscopic image of U-87 cancer cells when exposed to neutrons for 40 minutes ($2\times10^{12}$ n/cm$^2$)
Figure 9C:
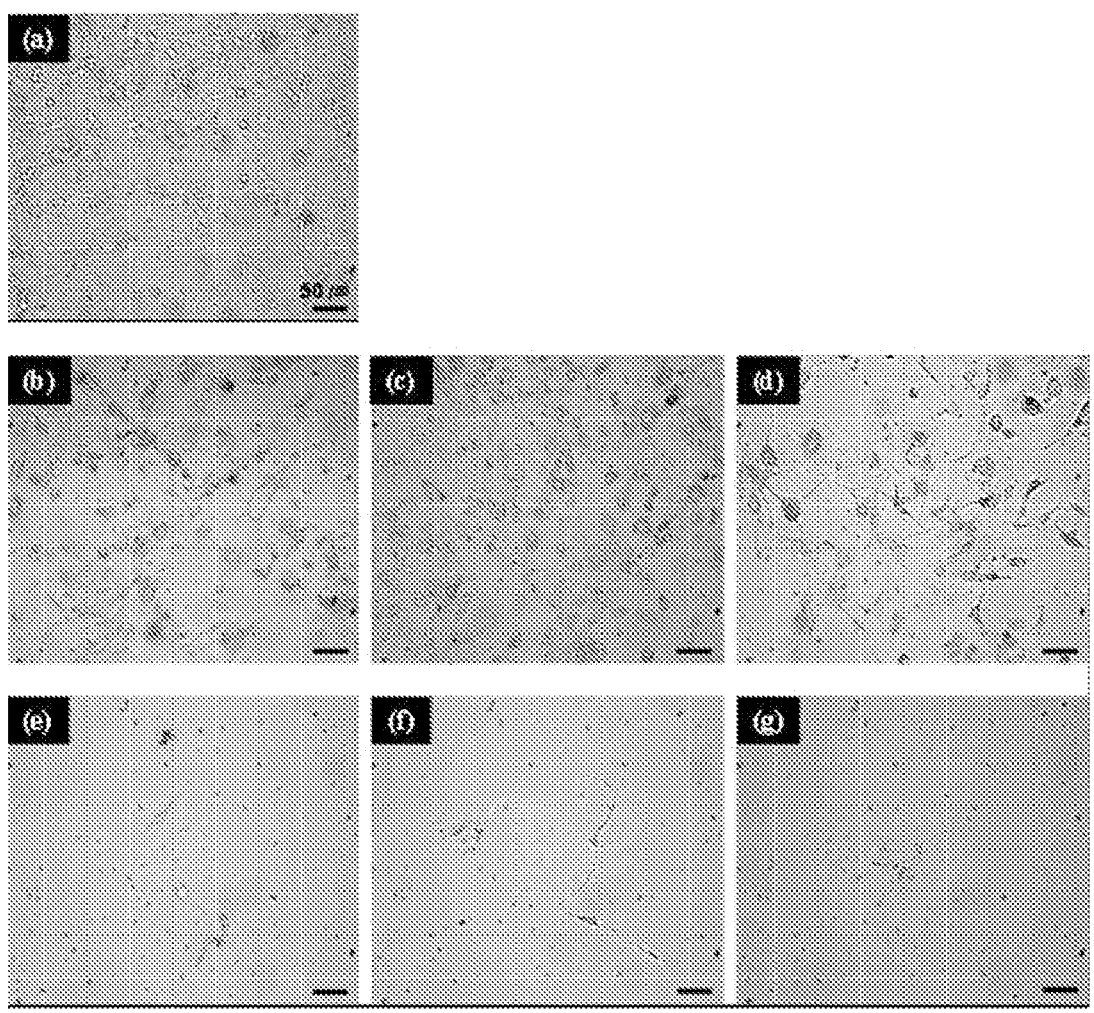
FIG. 9C shows a microscopic image of U-87 cancer cells when exposed to neutrons for 60 minutes ($3\times10^{12}$ n/cm$^2$), wherein, in FIGS. 9A through 9C, (a) is an image of a control group, that is, U-87 cells which were not treated with any compound; (b), (c), and (d) are images of U-87 cells treated with $^{10}$BSH at a boron concentration of 30, 45, and 60 μg/mL, respectively; and (e), (f), and (g) are images of U-87 cells treated with $^{10}$BSH-LDH at boron concentrations of 30, 45, and 60 μg/mL, respectively.

Each group was identified with an optical microscope. The results are shown in FIGS. 9A through 9C. FIG. 9A shows microscopic images of U-87 brain cancer cells when exposed to neutrons for 20 minutes (corresponding to the thermal neutron flux of 1×$10^{12}$ n/$cm^2$). FIG. 9B shows microscopic images of U-87 brain cancer cells when exposed to neutrons for 40 minutes (corresponding to the thermal neutron flux of 2×$10^{12}$ n/$cm^2$). FIG. 9C shows microscopic images of U-87 brain cancer cells when exposed to neutrons for 60 minutes (corresponding to the thermal neutron flux of 3×$10^{12}$ n/$cm^2$). Referring to FIGS. 9A through 9C, (a) is an image of U-87 brain cancer cells which were not treated with any compound, that is, a control group; (b), (c), and (d) are images of U-87 brain cancer cells treated with $^{10}$BSH at boron concentrations of 30, 45, and 60 μg/mL, respectively; and (e), (f), and (g) are images of U-87 brain cancer cells treated with $^{10}$BSH-LDH at the boron concentrations of 30, 45, and 60 μg/mL, respectively.

Referring to FIGS. 9A through 9C, the survival rate of U-87 brain cancer cells treated with $^{10}$BSH was very different from the survival rate of U-87 brain cancer cells treated with $^{10}$BSH-LDH. All the images were obtained 10 days after neutrons were irradiated to cells. The survival rate of U-87 brain cancer cells treated with $^{10}$BSH was similar to the survival rate of the control group at each thermal neutron flux. On the other hand, no living cells appeared in the images of U-87 brain cancer cells treated with $^{10}$BSH-LDH.

As described above, a boron compound-LDH nanohybrid according to the present invention has a high level of cell membrane permeability with respect to cancer cells and a high level of selectivity with respect to cancer cells, and therefore, can be effectively used even in a small amount for boron neutron capture therapy without cytotoxicity with respect to a normal cell.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A nanohybrid of a boron compound with non-toxic layered double hydroxide (LDH), wherein the boron compound is hybridized by being intercalated in between layers of the LDH.

2. The nanohybrid of claim 1, wherein the LDH comprises a bivalent metal and a trivalent metal, wherein the bivalent metal is selected from the group consisting of $Mg^{2+}$, $Ca^{2+}$, $Zn^{2+}$, and a combination thereof, and the trivalent metal is selected from the group consisting of $Al^{3+}$, $Fe^{3+}$, and a combination thereof.

3. The nanohybrid of claim 1, wherein the boron compound is selected from the group consisting of mecaptoundecahydro-closo-dodecaborate (BSH), borono-phenylalanine (BPA), an o-carborane-1,2-dicarboxylic acid, a p-carborane-1,12-dicarboxylic acid, and a combination thereof.

4. The nanohybrid of claim 1, wherein the particle size of the boron compound-LDH nanohybrid is in a range of 100 to 300 nm.

5. A method of preparing the nanohybrid of claim 1, the method comprising:
dissolving the boron compound for boron neutron capture therapy in a base solution; and
adding dropwise an aqueous solution comprising a bivalent metal salt and a trivalent metal salt to the resultant boron solution until a pH of the resultant solution is in a range of 7 to 9.

6. The method of claim 5, wherein the base solution comprises an aqueous solution of sodium hydroxide or ammonia.

7. The method of claim 5, wherein the bivalent metal salt is selected from the group consisting of zinc nitrate, zinc chloride, magnesium nitrate, and magnesium chloride, and the trivalent metal salt is selected from the group consisting of aluminum nitrate and aluminum chloride.

8. A pharmaceutical composition for boron neutron capture therapy, comprising the nanohybrid of claim 1.

* * * * *